United States Patent [19]

Shishido

[11] 4,309,500
[45] Jan. 5, 1982

[54] SILVER HALIDE COLOR PHOTOGRAPHIC LIGHT-SENSITIVE MATERIAL

[75] Inventor: Tadao Shishido, Minami-ashigara, Japan

[73] Assignee: Fuji Photo Film Co., Ltd., Kanagawa, Japan

[21] Appl. No.: 40,822

[22] Filed: May 21, 1979

Related U.S. Application Data

[63] Continuation-in-part of Ser. No. 874,086, Feb. 1, 1978, abandoned.

[30] Foreign Application Priority Data

Feb. 4, 1977 [JP] Japan .................................. 52-11366

[51] Int. Cl.³ .............................................. G03C 1/84
[52] U.S. Cl. ..................................... 430/507; 430/517; 430/543; 430/552; 430/554; 430/560; 430/522; 430/512; 542/427; 542/438; 548/218
[58] Field of Search .............. 96/84 UV, 74, 100, 120, 96/139; 430/522, 560, 512, 543, 570, 552, 591, 554, 507, 558, 560, 559, 517; 542/427, 438; 548/218

[56] References Cited

U.S. PATENT DOCUMENTS

| | | | |
|---|---|---|---|
| 2,252,718 | 8/1941 | Mannes et al. ........................ | 96/59 |
| 2,956,879 | 10/1960 | Campen ............................... | 96/74 |
| 3,523,953 | 8/1970 | Strobel et al. ....................... | 252/300 |
| 3,629,274 | 12/1974 | Oliver .................................. | 96/120 |
| 3,652,284 | 3/1972 | Oliver .................................. | 430/522 |
| 3,694,211 | 9/1972 | Sato et al. ........................... | 96/84 UV |
| 3,707,375 | 12/1972 | Ohi et al. ............................. | 96/84 UV |
| 3,873,323 | 3/1975 | Nakamura et al. ................... | 96/120 |
| 4,015,988 | 4/1977 | Shiba et al. .......................... | 96/74 |
| 4,163,671 | 8/1979 | Inoue et al. .......................... | 96/84 UV |

*Primary Examiner*—Won H. Louie, Jr.
*Attorney, Agent, or Firm*—Sughrue, Mion, Zinn, Macpeak & Seas

[57] ABSTRACT

A silver halide color photographic light-sensitive material which contains at least one compound represented by the following general formula (I):

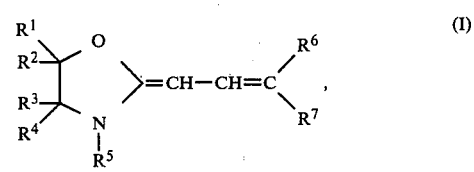

wherein $R^1$, $R^2$, $R^3$ and $R^4$, which may be the same or different, each represents a hydrogen atom or an aliphatic group; $R^5$ represents an aliphatic group or an aromatic group, $R^6$ and $R^7$, which may be the same or different, each represents a cyano group, a $-COR^8$ group, a $-COOR^8$ group or a $-SO_2R^9$ group; and $R^8$ represents an aliphatic group and $R^9$ represents an aliphatic group or an aromatic group. The silver halide color photographic light-sensitive material has improved color reproduction which is not affected by differences in the ultraviolet light absorption characteristics of the camera lens.

10 Claims, No Drawings

SILVER HALIDE COLOR PHOTOGRAPHIC LIGHT-SENSITIVE MATERIAL

This application is a continuation-in-part of application Ser. No. 874,086 filed Feb. 1, 1978, now abandoned.

BACKGROUND OF THE INVENTION

1. Field of the Invention

The present invention relates to a silver halide color photographic light-sensitive material, particularly, to a silver halide color photographic light-sensitive material having improved color reproduction which is not affected by differences in the ultraviolet light absorption characteristics of the camera lens. Further, the present invention relates to a method of minimizing variations in color balance caused by differences in the ultraviolet light absorption of the camera lens.

2. Description of the Prior Art

Lenses which are coated with an ultraviolet light absorbing agent or lenses which are not coated with an ultraviolet light absorbing agent are used in commercially available cameras, e.g., as disclosed in Japanese Patent Application Nos. (OPI) 56620/1976 and 49029/1977, U.S. Pat. Nos. 3,629,274, 3,486,897, 4,045,229, 3,652,284, 3,770,757, 3,215,530, 3,707,375, 3,705,805, 3,352,681, 3,278,448, 3,253,921, and 3,738,837, Japanese Patent Publication No. 26138/1974, and 25337/1975, British Pat. No. 1,338,265, etc.

When an object is photographed using these two kinds of lenses under the same conditions and the silver halide photographic light-sensitive materials thus exposed are processed under the same conditions, the resulting photographic images generally have different color tones. This phenomenon results from the fact that the percent transmission of ultraviolet light of the lens and the wavelength range of light absorbed by the lens vary depending on the presence or absence of an ultraviolet light absorbing agent.

SUMMARY OF THE INVENTION

Accordingly, an object of the present invention is to provide a silver halide color photographic light-sensitive material having improved color reproduction which is not affected by differences in the ultraviolet light absorption characteristics of the camera lens.

Another object of the present invention is to provide a silver halide photographic light-sensitive material showing less variations in color balance with various camera lenses and whose photographic properties, such as sensitivity, fog, etc., are not adversely affected by differences in camera lenses.

A further object of the present invention is to provide a method of reducing variations in the color balance of silver halide color photographic light-sensitive materials.

The above described objects of the present invention have been effectively attained by adding at least one ultraviolet light absorbing agent represented by the following general formula (I)

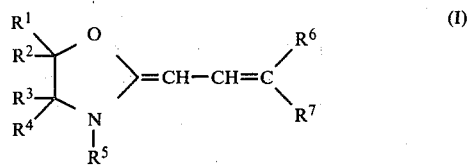

wherein $R^1$, $R^2$, $R^3$ and $R^4$, which may be the same or different, each represents a hydrogen atom or an aliphatic group; $R^5$ represents an aliphatic group or an aromatic group; $R^6$ and $R^7$, which may be the same or different, each represents a cyano group, a $-COR^8$ group, a $-COOR^8$ group, or a $-SO_2R^9$ group; $R^8$ represents an aliphatic group; and $R^9$ represents an aliphatic group or an aromatic group, said compound having an absorption maximum at about 360 to 375 mμ; to a silver halide color photographic light-sensitive material.

DETAILED DESCRIPTION OF THE INVENTION

In the above formula, $R^1$, $R^2$, $R^3$ and $R^4$, which may be the same or different, each represents a hydrogen atom or an aliphatic group [for example, a straight chain or branched chain alkly group having 1 to 18, preferably 1 to 10, carbon atoms, an alkenyl group having 3 to 10 carbon atoms, a substituted alkyl group having 1 to 20, preferably 3 to 20, total carbon atoms which can be substituted with one or more of, for example, a hydroxy group, an aryl group, a carboxy group, a sulfo group, an alkoxycarbonyl group having 1 to 4 carbon atoms in the alkyl moiety thereof, etc., or the like, and more specifically, a methyl group, an ethyl group, a hydroxyethyl group, an isopropyl group, a t-butyl group, an iso-butyl group, a 2-ethylhexyl group, a decyl group, a dodecyl group, an octadecyl group, a carboxyethyl group, an ethoxycarbonylethyl group, a sulfopropyl group, a benzyl group, a phenethyl group, an allyl group, etc.] $R^5$ represents an aliphatic group having 1 to 20, preferably 1 to 10, carbon atoms (for example, the groups described above for $R^1$ to $R^4$) or an aromatic group (preferably, an aryl group having 6 to 20, preferably 6 to 12, carbon atoms, in which the aromatic ring(s) can be substituted with one or more substituents (for example, an alkyl group, preferably having 1 to 4 carbon atoms, an alkoxy group having 1 to 8 carbon atoms, a halogen atom such as a chlorine atom, a bromine atom, a fluorine atom, etc.) and more specifically, a phenyl group, a p-methoxyphenyl group, a m-chlorophenyl group, a p-hexyloxyphenyl group, an o-methoxyphenyl group, a p-ethoxyphenyl group, an o-methylphenyl group, an m-ethylphenyl group, a p-t-butylphenyl group, and a p-n-propylphenyl group, etc.). $R^6$ and $R^7$, which may be the same or different, each represents a cyano group, a $-COR^8$ group, a $-COOR^8$ group or a $-SO_2R^9$ group, and $R^8$ represents an aliphatic group (for example, the aliphatic groups described above for $R^5$, such as an alkyl group, a substituted alkyl group, etc., more specifically, a methyl group, an ethyl group, an n-propyl group, an isopropyl group, an n-butyl group, a t-butyl group, an amyl group, an isoamyl group, a t-amyl group, an n-hexyl group, a 2-ethylhexyl group, an n-octyl group, an n-decyl group, a dodecyl group, a tetradecyl group, a hexadecyl group, an octadecyl group, a hyroxyethyl group, a benzyl group, or a phenethyl group. $R^9$ represents an aliphatic group as described above for $R^8$ or an aromatic group such as a phenyl group, an o-methylphenyl group, a p-methylphenyl group, an m-ethylphenyl group, a p-t-butylphenyl group, a p-n-propylphenyl group, an o-methoxyphenyl group, a p-ethoxyphenyl group, a p-methoxyphenyl group, an m-chlorophenyl group, an o-chlorophenyl group, a p-chlorophenyl group, a p-bromophenyl group, an m-bromophenyl group, and a p-hexyloxyphenyl group, etc.

Preferred compounds according to the present invention useful as ultraviolet light absorbing agents have an absorption maximum at about 360 to 375 mμ and are selected from those represented by the following general formula (II):

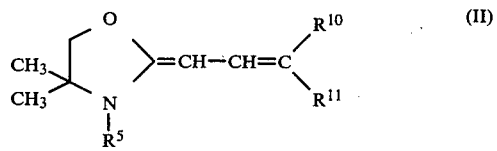

wherein $R^5$ has the same meaning as defined in the general formula (I); and $R^{10}$ and $R^{11}$, which may be the same or different, each represents a cyano group, a $-COR^{12}$ group, a $-COOR^{12}$ group, or a $-SO_2R^{13}$ group; $R^{12}$ represents an aliphatic group as described above for $R^8$, and more preferably represents an alkyl group; and $R^{13}$ represents an aliphatic group as described above for $R^8$ or an aromatic group as described above for $R^5$ with more preferred examples being an alkyl group and an unsubstituted or substituted phenyl group wherein the substituent is, for example, an alkyl group, an alkoxy group or a halogen atom.

The following advantages are achieved with the use of the ultraviolet light absorbing agents according to the present invention:

(1) They effectively absorb ultraviolet light of a wavelength of about 300 to 400 mμ and do substantially not absorb visible light;

(2) Their color is not changed upon development processing;

(3) They do not have adverse influences upon photographic light-sensitive materials on preparation, during storage or at the development processing thereof.

(4) They can be dispersed in a finely divided emulsified state into a hydrophilic colloid solution (for example, a gelatin sol) in the presence of or absence of a small amount of a water-insoluble organic solvent having a high boiling point and they have properties such that an emulsified dispersion thereof is stable. Further, they do not cause a reduction in transparency of the photographic hydrophilic colloid layers or hardly soften the layers.

(5) They prevent fog (static marks) caused by the ultraviolet light emitted by charging due to friction on a light-sensitive material when they are incorporated in, for example, a back layer, a subbing layer, an interlayer, a transparent support, a surface protective layer and a light-sensitive emulsion layer which is to be covered therewith.

(6) They prevent the discoloration of a positive color image on a color paper or a color diffusion transfer film unit due to ultraviolet light when they are incorporated in, for example, a mordanting layer.

The ultraviolet light absorbing agents according to the present invention can be used individually or as a mixture of two or more thereof.

Typical examples of compounds represented by the above described general formula (I) of the present invention useful as ultraviolet light absorbing agents and their absorption maximum wavelength are described below. (The absorption maximum wavelength thereof was measured at a concentration of $1 \times 10^{-5}$ mol/l in methanol at 25° C.):

Compound (I-1)

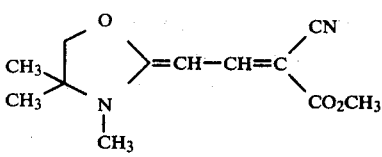

$\lambda_{max}^{MeOH}$ 372 mμ

Compound (I-2)

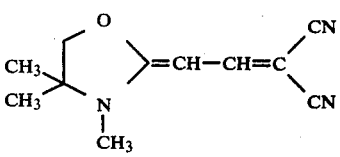

$\lambda_{max}^{MeOH}$ 368 mμ

Compound (I-3)

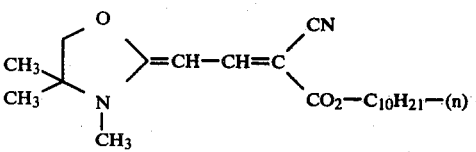

$\lambda_{max}^{MeOH}$ 374 mμ

Compound (I-6)

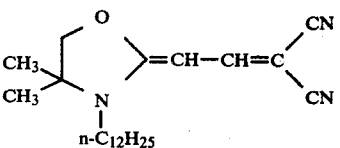

$\lambda_{max}^{MeOH}$ 372 mμ

Compound (I-7)

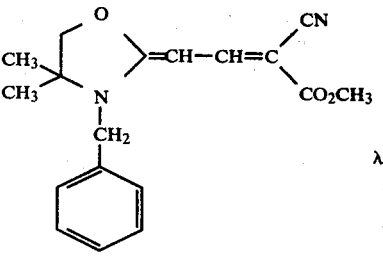

$\lambda_{max}^{MeOH}$ 375 mμ

Compound (I-8)

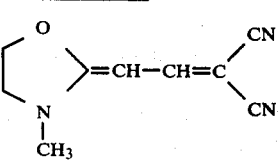

$\lambda_{max}^{MeOH}$ 370 mμ

Compound (I-9)

-continued

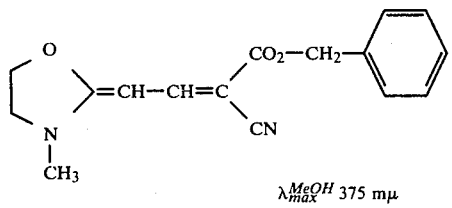

Compound (I-10)

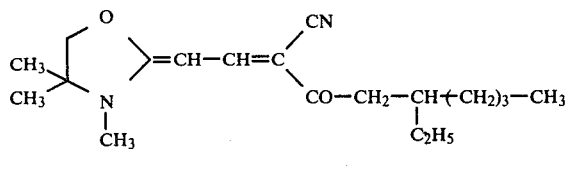

Compound (I-11)

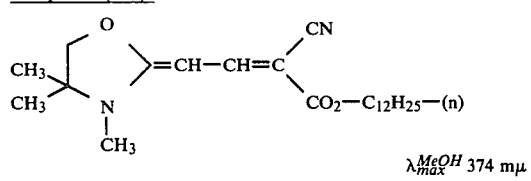

Compound (I-12)

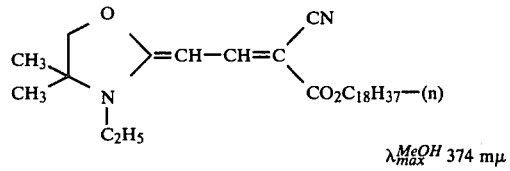

Compound (I-13)

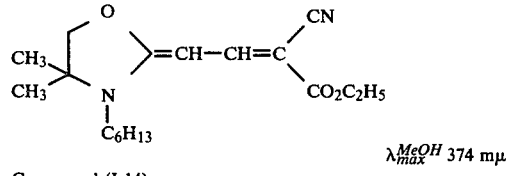

Compound (I-14)

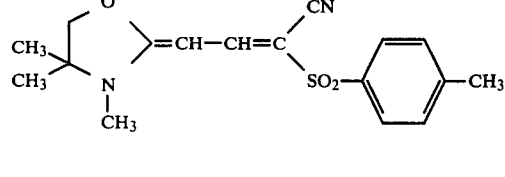

The compounds of the general formula (I) which are novel compounds can be synthesized by reacting an oxazolium salt as a starting material and from about 1 to about 3 moles of an active methylene compound per mol of the oxazolium salt in the presence of from about 1 to about 2 equivalents of a neutralizing agent per equivalent of the oxazolium salt in a suitable solvent on heating at a temperature of about 40° to about 100° C.

Suitable examples of neutralizing agents which can be used include triethylamine, sodium bicarbonate, sodium carbonate, sodium hydroxide, potassium hydroxide, ammonia, diaminobicyclooctane, etc.

Suitable examples of solvents which can be employed include methanol, ethanol, isopropanol, ethyl acetate, dimethylformamide, methyl Cellosolve, etc., and a suitable amount of the solvent ranges from about 1 to about 20 times by weight to the weight of the oxazolium salt.

Specific examples of the synthesis of typical ultraviolet light absorbing agents according to the present invention are described below. Other compounds can be easily synthesized in a similar manner. Unless otherwise indicated herein all parts, percents, ratios and the like are by weight.

SYNTHESIS EXAMPLE 1

(Synthesis of Compound I-1)

20 g of 2-(2-N-acylanilinovinyl)-3,4,4-trimethylbenzoxazolium iodide, 7 g of methyl cyanoacetate and 7 g of triethylamine were added to 50 ml of methanol. The mixture was refluxed with heating for 2 hours. 25 ml of methanol was then removed by distillation under reduced pressure. To the residue, 25 ml of ethyl acetate was added and the mixture was cooled to 5° C. with ice. The resultant crystals were collected by filtration and recrystallized from ethyl acetate. 6 g of needle-like crystals having a melting point of 169° C. were obtained.

SYNTHESIS EXAMPLE 2

(Synthesis of Compound I-3)

40 g of 2-(2-N-acylanilinovinyl)-3,4,4-trimethylbenzoxazolium iodide, 21 g of n-decyl cyanoacetate and 12 g of triethylamine were added to 50 ml of methanol. The mixture was refluxed with heating for 2 hours. Methanol was then removed by distillation under reduced pressure. To the residue, 50 ml of benzene was added and the resultant crystals were removed by filtration. The filtrate was distilled under reduced pressure to remove the benzene. 42 g of the resultant oily product was chromatographically separated using 900 g of silica gel (Kieselgel 60, produced by Merck Co.) and benzene as an eluant. 15 g of wax-like Compound I-3 was obtained.

It is preferred for the compounds of the present invention incorporated in a color photographic material to substantially not absorb visible light and to have an absorption maximum at about 360 to 375 m$\mu$ in order to effectively absorb ultraviolet light of a wavelength of 300 to 400 m$\mu$.

The compounds of the present invention can be added to photographic hydrophilic colloid layers by dissolving them in a substantially water insoluble organic solvent having a high boiling point and emulsifying or by dispersing them directly (for example, using the methods described in U.S. Pat. Nos. 2,739,888 and 3,352,681). Further, the compounds can be added by dispersing them using a latex described in Japanese Patent Application (OPI) No. 59943/1976. Furthermore, the compounds which are water soluble can be added to the hydrophilic colloid layers by dissolving them in water and adding the aqueous solution to an aqueous hydrophilic colloid solution.

The compounds of the present invention are incorporated in photographic elements of color light-sensitive materials. For example, they may be added to a protective layer, a light-sensitive silver halide emulsion layer, a yellow filter layer, an intermediate layer, a subbing layer, a back layer, a transparent support, a cover sheet, a neutralizing layer, a neutralization rate controlling layer, a mordanting layer, etc. However, it is preferred to add them to a photographic layer closer to the incident light exposure side of the light-sensitive materials.

The amount of the compounds according to the present invention which can be used in the layer is generally above about $1\times 10^{-4}$ g/m$^2$ (as the total amount when the compounds are added to two or more layers). Although the maximum amount of the compound represented by the general formula (I) is not limited and basically is determined from an economical standpoint, such generally can be employed in an amount up to about 10 g/m$^2$. Preferred amounts of the compounds can be suitably determined using well known testing methods.

Examples of substantially water insoluble organic solvents having a high boiling point which can be used for dispersing the compounds of the present invention include alkyl esters of phthalic acid (for example, dibutyl phthalate or dioctyl phthalate, etc.), trimellitic acid esters (for example, tri-t-octyl trimellitate, etc.), aromatic ethers (for example, di-m-tolyl ether, 1,3-dibutoxybenzene, 1,3-dioctyloxybenzene, 2,4-di-t-amyl-phenoxyhexane, 2,4-di-nonylphenoxybutane, etc.), phosphoric acid esters (for example, diphenyl phosphate, triphenyl phosphate, tricresyl phosphate or dioctylbutyl phosphate, etc.), citric acid esters (for example, tributyl acetylcitrate, etc.), and alkylamides (for example, N,N-diethyllaurylamide, etc.), etc.

Hydrophilic colloid materials which can be used for the photographic layers and particularly for the hydrophilic colloid layers in the silver halide photographic lightsensitive materials include many known materials such as gelatin, gelatin derivatives such as phthalated gelatin, etc., carboxycellulose derivatives, sulfocellulose derivatives, polyacrylamides, polyvinyl alcohol and polyvinyl pyrrolidone, etc.

The compounds of the present invention may be used together with a known photographic antioxidant (for example, a hydroquinone derivative, a catechol derivative, an aminophenol derivative and a gallic acid derivative, etc.) or a known photographic ultraviolet light absorbing agent such as a benzotriazole type compound or a benzophenone type compound under conditions which satisfy the above described objects of the present invention. The amount of known ultraviolet light-absorbing agents used ranges from about $1\times 10^{-4}$ to 10 g/m$^2$.

Various kinds of additives and various kinds of photographic layers such as a silver halide emulsion layer, a protective layer, a filter layer, an intermediate layer, a subbing layer and a back layer, etc. as described in U.S. Pat. Nos. 4,028,112, 4,047,964, and 3,966,477, British Pat. No. 1,466,836, etc. can be present in the silver halide color light-sensitive materials of the present invention.

Suitable supports which may be used are, for example, a film of polyethylene terephthalate, polycarbonate, polystyrene, polypropylene or cellulose acetate, etc., a polyethylene laminated paper or a baryta paper.

Silver bromide, silver chloride, silver iodobromide, silver chlorobromide or silver chloroiodobromide, etc. may be used as the silver halide for the silver halide emulsion. The silver halide emulsion can be produced using any known process.

The silver halide emulsion may be sensitized using a chemical sensitizing agent (for example, a sulfur sensitizing agent such as thiourea, allylthiocarbamide, allylisothiocyanate or cystine, etc., a gold compound such as potassium chloroaurate, auric trichloride or potassium auric thiocyanate, etc., and other noble metal sensitizing agent, and a known reduction sensitizing agent, etc.).

Further, a known stabilizing agent or an anti-fogging agent such as a triazole, an imidazole or an azaindene may be added to the silver halide emulsion, if desired.

Moreover, various color image forming compounds can be used for the color photographic sensitive materials of the present invention. Examples thereof include benzoylacetoanilide type and pivaloylacetoanilide type 2-equivalent or 4-equivalent yellow couplers, pyrazolone type, indazolone type or cyanoacetyl type 2-equivalent or 4-equivalent magenta couplers, phenol type or naphthol type 2-equivalent or 4-equivalent cyan couplers and cyan or magenta colored couplers (the above described 2-equivalent yellow, magenta or cyan couplers may be a DIR coupler, if desired). It is preferred for these couplers be diffusion resistant. Further, a redox compound which releases a diffusible dye, a coupler which releases a diffusible dye or a dye developer, etc., may be used.

In addition, known additives (for example, spectral sensitizing agent, color stain preventing agents, color fading preventing agents, hardening agents, surface active agents or antistatic agents, etc.) may be added, if desired.

Suitable examples of layer structures of the silver halide color light-sensitive materials of the present invention are described below.

(1) A multilayer color light-sensitive material which is prepared by applying to a support, in order, an antihalation layer, a gelatin intermediate layer, a red-sensitive silver halide emulsion layer (which may be composed of a single layer or may have a multilayer structure comprising a fine grain silver halide emulsion layer having a comparatively low sensitivity and a fine grain silver halide emulsion layer having a higher sensitivity thereon, or a multilayer structure comprising three or more such layers), a gelatin intermediate layer, a green-sensitive silver halide emulsion layer (which may be composed of a single layer or may have a multilayer structure as described for the red-sensitive silver halide emulsion layer), a yellow filter layer, a blue-sensitive silver halide emulsion layer (which may be composed of a single layer or may have a multilayer structure) and a protective layer, which is suitable as a high speed color negative film;

(2) A multilayer color light-sensitive material which is prepared by applying to a support, in order, an antihalation layer, a gelatin intermediate layer, red-sensitive silver halide emulsion layers (i.e., a red-sensitive silver halide emulsion layer having a higher sensitivity and a red-sensitive silver halide emulsion layer having a comparatively low sensitivity thereon), a gelatin intermediate layer, a green-sensitive silver halide emulsion layer having a high sensitivity, a yellow filter layer, a blue-sensitive silver halide emulsion layer, a green-sensitive silver halide emulsion layer having a comparatively low sensitivity and a protective layer, which is suitable as a high speed color reversal film;

(3) A multilayer color light-sensitive material which is prepared by applying to a support, in order, an antihalation layer, a gelatin intermediate layer, a blue-sensitive silver halide emulsion layer, a gelatin intermediate layer, a red-sensitive silver halide emulsion layer, a gelatin intermediate layer, a green-sensitive silver halide emulsion layer, a yellow filter layer and a protective layer, which is suitable as an 8 mm color film.

In a color light-sensitive material having layer structure (1), the compound of the present invention is preferably added to at least one of the protective layer, the blue-sensitive silver halide emulsion layer having a higher sensitivity or the blue-sensitive silver halide emulsion layer having a comparatively low sensitivity.

In a color light-sensitive material having layer structure (2), the compound of the present invention is preferably added to at least one of the protective layer, the green-sensitive silver halide emulsion layer having a comparatively low sensitivity or the blue-sensitive silver halide emulsion layer, and, particularly, at least one of the protective layer and the green-sensitive silver halide emulsion layer having a comparatively low sensitivity.

In a color light-sensitive material having layer structure (3) although the compound of the present invention may be added to any layer, it is more preferred to add the compound of the present invention to at least one of the protective layer, the yellow filter layer or the green-sensitive silver halide emulsion layer.

Examples of silver halide color photographic light-sensitive materials to which the present invention is applicable include color negative films, color reversal films, color positive films, color papers, color direct positive films and diffusion transfer color light-sensitive materials (using negative emulsions or direct positive emulsions which are subjected to fogging treatment after exposure), etc.

It goes without saying that the compound of the present invention can be used for light-sensitive materials having layer structures other than the above described layer structures.

The silver halide light-sensitive materials of the present invention can be processed using any conventional development processing or using a DTR (diffusible dye transfer reversal) color processing solution included in the light-sensitive material. For example, the process described in *Journal of the Society of Motion Picture and Television Engineers*, Volume 61, (1953), pages 667 to 701, U.S. Pat. No. 4,028,112, etc. can be used.

Suitable examples of light sources which can be used for exposure include sunlight, a tungsten lamp, a fluorescent lamp, a mercury lamp, a xenon arc lamp, a carbon arc lamp, a xenon flash lamp, a cathode ray tube flying spot, etc. The exposure time used is not in particular limited.

With the silver halide color light-sensitive material of the present invention, there are no variations in the color reproduction due to differences in the ultraviolet light absorption of the camera lens used. Further, photographic properties such as sensitivity or fog are not adversely affected and there is no fog due to the generation of static charges which are formed during production or storage of the light-sensitive materials.

The present invention will now be illustrated in greater detail by the following examples.

EXAMPLE 1

As illustrated in Table 1 below, to a mixture of 1,000 g of a 10% aqueous solution of gelatin and 75 ml of a 5% aqueous solution of sodium dodecylbenzene sulfonate, 40 ml of dibutyl phthalate, 100 ml of ethyl acetate and 20 ml of a 20% solution of sorbitan monolaurate in methanol were added and dispersed using a colloid mill for 5 minutes to produce Emulsified Dispersion A, which was used as a control.

120 g of Compound (I-2) was dispersed together with the same components of Emulsified Dispersion A in the same manner as described above to produce Emulsified Dispersion B. Similarly, Emulsified Dispersion C containing 120 g of Compound (I-3), Emulsified Dispersion D containing 120 g of Compound (I-14), Emulsified Dispersion E containing 120 g of Compound (I-1), Emulsified Dispersion F containing 100 g of Compound (I-2) and 20 g of 2-(2-hydroxy-5-tert-butyl)phenylbenzotriazole and as a comparison dispersion, Emulsified Dispersion G containing 120 g of 2-(3-cyano-3-dodecylsulfonylallylidene)-3-ethylbenzoxazoline,* Emulsified Dispersion H containing 120 g of 2-(3-cyano-3-dodecylsulfonylallylidene)-3-ethylthiazolidine, Emulsified Dispersion I containing 120 g of 2-(3-cyano-3-dodecylsulfonylallylidene)-3-(3-sulfopropyl)-thiazolidine, potassium salt* and Emulsified Dispersion J containing 120 g of n-decyl 4-methoxy-α-cyanocinnamate were prepared.

\* Compound disclosed in Example 2 of U.S. Pat. No. 3,629,274 (Oliver).
\*\* Compound disclosed in Example 3 of U.S. Pat. No. 3,629,274 (Oliver).
\*\*\* Compound disclosed in Example 9 of U.S. Pat. No. 3,629,274 (Oliver).

TABLE 1

| | Emulsified Dispersion | | | | | | | | | |
|---|---|---|---|---|---|---|---|---|---|---|
| | A | B | C | D | E | F | G | H | I | J |
| Gelatin (10% aq. soln.) | 1,000 g | 1,000 g | 1,000 g | 1,000 g | 1,000 g | 1,000 g | 1,000 g | 1,000 g | 1,000 g | 1,000 g |
| Sodium dodecylbenzene sulfonate (5% aq. soln.) | 75 ml | 75 ml | 75 ml | 75 ml | 75 ml | 75 ml | 75 ml | 75 ml | 75 ml | 75 ml |
| Dibutyl phthalate | 40 ml | 40 ml | 40 ml | 40 ml | 40 ml | 40 ml | 40 ml | 40 ml | 40 ml | 40 ml |
| Ethyl acetate | 100 ml | 100 ml | 100 ml | 100 ml | 100 ml | 100 ml | 100 ml | 100 ml | 100 ml | 100 ml |
| 20 % Solution of Sorbitan monolaurate (20% methanol soln.) | 20 ml | 20 ml | 20 ml | 20 ml | 20 ml | 20 ml | 20 ml | 20 ml | 20 ml | 20 ml |
| Compound (I-2) | — | 120 g | — | — | — | 100 g | — | — | — | — |
| Compound (I-3) | — | — | 120 g | — | — | — | — | — | — | — |
| Compound (I-14) | — | — | — | 120 g | — | — | — | — | — | — |
| Compound (I-1) | — | — | — | — | 120 g | — | — | — | — | — |
| 2-(2-Hydroxy-5-tert-butyl)-phenylbenzotriazole | — | — | — | — | — | 20 g | — | — | — | — |
| Compound in Example 2 of Oliver | — | — | — | — | — | — | 120 g | — | — | — |
| Compound in Example 3 of Oliver | — | — | — | — | — | — | — | 120 g | — | — |
| Compound in Example 9 of Oliver | — | — | — | — | — | — | — | — | 120 g | — |
| n-Decyl 4-Methoxy-α-cyanocinnamate | — | — | — | — | — | — | — | — | — | 120 g |

The following layers were then applied to a support to produce samples.

First Layer

An antihalation layer containing the following dyes mordanted with a mordant:

| | Coating Amount |
|---|---|
| Cyan Dye | |
| NaO₃SH₂CNH O OH, SO₃Na, NaO₃S, OH O NHCH₂SO₃Na | about 200 mg/m² |
| Magenta Dye | |
| KOOC—C═C═(CH)₃—C—C—COOK, N, C═O, HO, C, N, N, (two p-SO₃K-phenyl groups on N) | about 200 mg/m² |
| Yellow Dye | |
| NaOOC—...CH═N═N—(phenyl)—SO₃Na, N, C, N, (phenyl)-SO₃Na | about 200 mg/m² |

Second Layer

A red-sensitive silver iodobromide (AgI: 4 mol%)-gelatin emulsion layer containing oil-soluble diffusion resistant cyan couplers of the formula

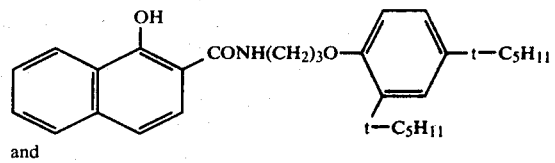

and

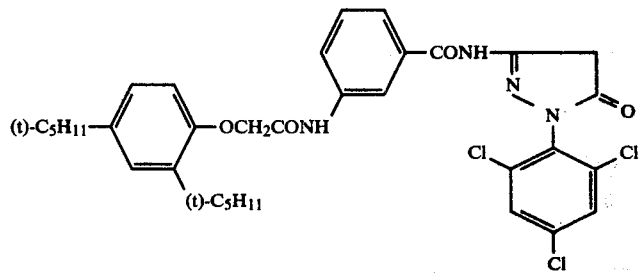

(molar ratio of silver/coupler: 25, amount of silver coated: 30 mg/100 cm²).

Third Layer

An intermediate layer containing gelatin (thickness: 1.5μ).

Fourth Layer

A green-sensitive silver iodobromide (AgI: 3.5 mol%)-gelatin emulsion layer containing diffusion resistant magenta couplers of the formula:

and

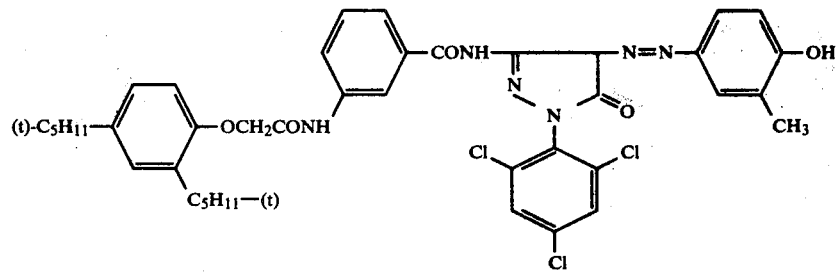

(molar ratio of silver/coupler: 35, amount of silver coated: 20 mg/100 cm²).

Fifth Layer

A gelatin layer having a yellow filter function with the same dyes and mordant as those of the First Layer.

Sixth Layer

A silver iodobromide (AgI: 3 mol%)-gelatin emulsion layer containing a diffusion resistant yellow coupler of the formula:

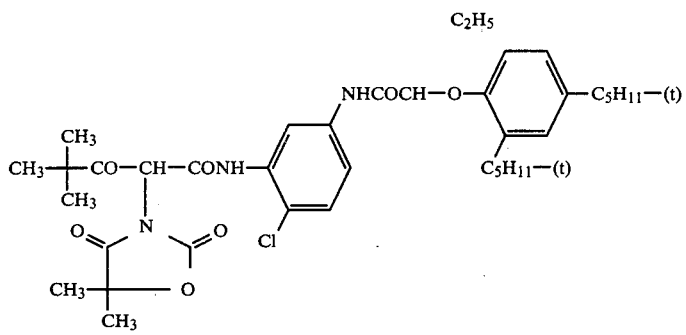

(molar ratio of silver/coupler: 10, amount of silver coated: 15 mg/100 cm$^2$).

Seventh Layer

A layer of the above described Emulsified Dispersion A applied in an amount of 1.93 g/m$^2$ (thickness of the layer: 1.8μ). This material was called Sample 1.

Similarly, Sample 2, Sample 3, Sample 4, Sample 5, Sample 6, Sample 7, Sample 8, Sample 9 and Sample 10 were produced using Emulsified Dispersion B, Emulsified Dispersion C, Emulsified Dispersion D, Emulsified Dispersion E, Emulsified Dispersion F, Emulsified Dispersion G, Emulsified Dispersion H, Emulsified Dispersion I and Emulsified Dispersion J, respectively, instead of Emulsified Dispersion A.

In order to measure variations in the color balance of the photographic light-sensitive materials caused by use of different kinds of camera lenses wherein the percent transmission of ultraviolet light different from lens to lens, a gray chart was photographed using a camera equipped with a lens of a high percent transmission of ultraviolet light and a camera equipped with the same lens as described above but having a filter which cut light of wavelengths below 390 mμ. After exposure, the samples were processed as described below.

The processing was carried out as follows:

| | Temperature (°C.) | Time |
|---|---|---|
| Color Develpoment | 38 | 3 min. and 15 sec. |
| Bleaching | " | 6 min. and 30 sec. |
| Water Wash | " | 3 min. and 15 sec. |
| Fixing | " | 6 min. and 30 sec. |
| Water Wash | " | 3 min. and 15 sec. |
| Stabilizing | " | 1 min. and 30 sec. |

The processing solutions employed had the following compositions.

| Color Developer solution: | |
|---|---|
| Water | 800 ml |
| Potassium Carbonate (anhydrous) | 38 g |
| Sodium Sulfite (anhydrous) | 4 g |
| Sodium Bromide | 1.5 g |
| Hydroxylamine Sulfate | 2.5 g |
| EDTA | 2.5 g |
| 4-[N-Ethyl-N-(β-ethoxyethyl)amino]-2-methylaniline Sulfate | 4.7 g |
| Water to make | 1 liter |
| | pH 10.0 |
| Bleaching Solution: | |
| Water | 600 ml |
| Ammonium Bromide | 150 g |
| EDTA-Fe(III) Sodium Salt | 100 g |
| Glacial Acetic Acid | 10 ml |
| EDTA | 10 g |
| Water to make | 1 liter |
| | pH 6.0 |
| Fixing Solution: | |
| Water | 800 ml |
| Ammonium Thiosulfate (70% aq. soln.) | 140 ml |
| Sodium Bisulfite (anhydrous) | 12 g |
| Water to make | 1 liter |
| Stabilizing Solution: | |
| Water | 800 ml |
| Formaldehyde (37% aq. soln.) | 5.0 ml |
| Polyethylene Glycol | 0.2 g |
| Ethylene Glycol | 2 g |
| Water to make | 1 liter |

The resultant negative images in both cases were then evaluated and the red light density measured, the green light density measured and the blue light density measured in both cases and compared with each other. The differences in the densities measured under each light are shown in Table 2 below.

TABLE 2

| Density[i] Difference | Sample | | | | | | | | | |
|---|---|---|---|---|---|---|---|---|---|---|
| | (1) | (2) | (3) | (4) | (5) | (6) | (7) | (8) | (9) | (10) |
| Red | 0 | 0 | 0 | 0 | 0 | 0 | 0 | 0 | 0 | 0 |
| Green | 0 | 0 | 0 | 0 | 0 | 0 | 0 | 0 | 0 | 0 |
| Blue | 0.14 | 0.07 | 0.06 | 0.06 | 0.06 | 0.07 | 0.05 | 0.07 | 0.06 | 0.12 |

[i]The values in Table 2 represent the difference between the image density in the case of photographing using a lens through which ultraviolet light completely passed and the image density in the case of photographing using the same lens equipped with a filter which cut light below 390 mμ (red, green or blue light density, as indicated).

In addition, the blue sensitivity of Samples 2 to 5 and 7 to 9 were compared with each other. The sensitometric results obtained are shown in Table 3 below.

TABLE 3

| | Sample | | | | | | |
|---|---|---|---|---|---|---|---|
| | (2) | (3) | (4) | (5) | (7) | (8) | (9) |
| Blue Relative[ii] | | | | | | | |

TABLE 3-continued

| | Sample | | | | | | |
|---|---|---|---|---|---|---|---|
| | (2) | (3) | (4) | (5) | (7) | (8) | (9) |
| Sensitivity | 100 | 100 | 100 | 100 | 80 | 85 | 85 |

(ii) The values in Table 3 represent a blue relative sensitivity provided that the blue sensitivity of Sample (2) is 100. The sensitometry was performed by photographing a gray chart by using the aforementioned camera equipped with the lens having a filter which cuts light of wavelengths below 390 mμ.

It can be understood from the results in Table 2 above that variations in blue density were less in the photographic light-sensitive materials using Compounds (I-1), (I-2), (I-3) and (I-14) (Samples 2 to 6), that the photographic light-sensitive materials are less affected by variations in the percent transmission of ultraviolet light and that the gray balance was excellent.

On the other hand, it is apparent from the results in Tables 2 and 3 above that the blue sensitivity is considerably reduced in Samples (7) to (9) using compounds disclosed in Oliver, as compared with those of Samples (2) to (5) of the present invention, even though the gray balance of Samples (7) to (9) is excellent as much as that of Samples (2) to (5). The decrease in blue sensitivity of Samples (7) to (9) is due to a considerable absorption of light in a visible wavelength region which also forms a color stain. The formation of color stain causes a seriously important problem when the compound disclosed in Oliver is incorporated in a color reversal film in particular.

The same results as those in Example 1 were also obtained when colloidal silver (about 4 mg/100 cm²) in the antihalation layer and/or colloidal silver (about 1 mg/100 cm²) in the filter layer was employed instead of the dye(s), respectively. Furthermore, the same results as those of Example 1 were also obtained when a gelatin layer without a yellow filter function was employed instead of the yellow filter layer.

EXAMPLE 2

The First Layer, the Second Layer, the Third Layer, the Fourth Layer and the Fifth Layer as described in Example 1 were provided in the same manner on a support as described in Example 1, and the Sixth Layer was produced as described below using emulsified dispersions described in Example 1. A protective layer of gelatin was coated on the Sixth Layer. In order to form the Sixth Layer, Emulsified Dispersion J was incorporated in an amount of 1.93 g/m² in the silver iodobromide emulsion and the blue-sensitive layer was applied in a dry thickness of 5.2μ to produce Sample 11. Emulsified Dispersion J in Sample 11 was replaced with Emulsified Dispersion B to produce Sample 12, and with Emulsified Dispersion C to produce Sample 13. These samples were exposed, processed and evaluated in the same manner as described in Example 1. The results obtained are shown in Table 4 below.

TABLE 4

| Density | Sample | | |
|---|---|---|---|
| Difference | (11) | (12) | (13) |
| Red | 0 | 0 | 0 |
| Green | 0 | 0 | 0 |
| Blue | 0.13 | 0.08 | 0.08 |

(The density difference in Table 4 has the same meaning as in Example 1.)

It can be understood from the results shown in Table 4 above that the compounds of the present invention have the effect of reducing variations in the color balance caused by differences in camera lenses, although they are added to the blue-sensitive layer.

EXAMPLE 3

Samples 1, 2 and 3 prepared as described in Example 1 were evaluated to determine the generation of static charges.

The protective layer of Samples 1, 2 and 3 was rubbed in a dark room with a rubber roll having a voltage in the triboelectric series of substantially 0 to cause light emission by discharging. These samples were simultaneously developed in the same manner as in Example 1 and the density of the static marks formed in each sample was measured. Increased blue density due to static marks was as shown in Table 5 below.

TABLE 5

| | Sample | | |
|---|---|---|---|
| Density | (1) | (2) | (3) |
| Red Density | 0 | 0 | 0 |
| Green Density | 0 | 0 | 0 |
| Blue Density | 1.0 | 0.2 | 0.1 |

(Red density, green density and blue density in Table 5 each means the image density measured under a red, green or blue light.)

It is clear from the results in Table 5 that the occurrence of static marks was reduced by the addition of the compounds of the present invention.

While the invention has been described in detail and with reference to specific embodiments thereof, it will be apparent to one skilled in the art that various changes and modifications can be made therein without departing from the spirit and scope thereof.

What is claimed is:

1. A silver halide color photographic light-sensitive material which contains at least one color image-forming compound, an ultraviolet light absorbing amount of at least one compound represented by the following general formula (I):

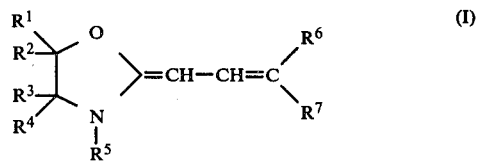

wherein $R^1$, $R^2$, $R^3$ and $R^4$, which may be the same or different, each represents a hydrogen atom or an aliphatic group selected from the group consisting of a straight chain or branched chain alkyl group having 1 to 18 carbon atoms, an alkenyl group having 3 to 10 carbon atoms and a substituted alkyl group having 1 to 20 total carbon atoms and substituted with one or more of a hydroxy group, an aryl group, a carboxy group, a sulfo group and an alkoxycarbonyl group; $R^5$ represents an aliphatic group selected from the group consisting of a straight chain or branched chain alkyl group having 1 to 20 carbon atoms, an alkenyl group having 3 to 10 carbon atoms and a substituted alkyl group having 1 to 20 total carbon atoms and substituted with one or more of the substituents as described above for the substituted alkyl group for $R^1$ to $R^4$, or an aromatic group; $R^6$ represents a cyano group and $R^7$ represents a cyano group, a —$COR^8$, A—$COOR^8$ group group or a —$SO_2R^9$ group; and $R^8$ represents an aliphatic group and $R^9$ represents an aliphatic group or an aromatic group wherein the aromatic group represented by $R^5$ or $R^9$ is an aryl group having 6 to 20 carbon atoms which may be substituted with one or more of an alkyl group, an alkoxy group and a halogen atom and wherein the aliphatic group represented by $R^8$ or $R^9$ is a straight chain or branched chain alkyl group having 1 to 20 carbon atoms, an alkenyl group having 3 to 20 carbon atoms or a substituted alkyl group having 1 to 20 total carbon atoms substituted with one or more of the substituents as described above for the substituted alkyl group for $R^1$ to $R^4$, said compound of the formula (I) having an absorption maximum at about 360 to 375 m$\mu$ and being capable of absorbing ultraviolet light of a wavelength of about 300 m$\mu$ to 400 m$\mu$ with substantially no absorbance of visible light.

2. The silver halide color photographic light-sensitive material as claimed in claim 1, wherein said ultraviolet light absorbing compound is represented by the following general formula (II):

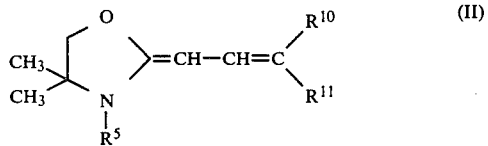

wherein $R^5$ has the same meaning as defined in the general formula (I); $R^{10}$ represents a cyano group and $R^{11}$ represents a cyano group, a —$COR^{12}$ group, a —$COOR^{12}$ group or a —$SO_2R^{13}$ group; and $R^{12}$ and $R^{13}$ each has the same meanings as those for $R^8$ and $R^9$, respectively.

3. The silver halide color photographic light-sensitive material as claimed in claim 1, wherein said compound of the formula (I) is present in an amount of at least about $1 \times 10^{-4}$ g/m$^2$.

4. The silver halide color photographic material as claimed in claim 1, which comprises a support having thereon at least one silver halide emulsion layer covered with a surface protective layer, and wherein at least one of the silver halide emulsion layer and the protective layer contains at least one compound represented by the general formula (I) as described in claim 1.

5. The silver halide color photographic light-sensitive material as claimed in claim 1, wherein said color photographic light-sensitive material is a multilayer color photographic light-sensitive material comprising a support having thereon an antihalation layer, an gelatin intermediate layer, a red-sensitive silver halide emulsion layer, a gelatin intermediate layer, a green-sensitive silver halide emulsion layer, a yellow filter layer, a blue-sensitive silver halide emulsion layer and a protective layer, and at least one of said blue-sensitive silver halide emulsion layer and said protective layer contains at least one compound represented by the general formula (I) as described in claim 1.

6. The silver halide color photographic light-sensitive material as claimed in claim 1, wherein said color photographic light-sensitive material is a multilayer color photographic light-sensitive material comprising a support having thereon an antihalation layer, a gelatin intermediate layer, a red-sensitive silver halide emulsion layer having a comparatively low sensitivity, a gelatin intermediate layer, a green-sensitive silver halide emulsion layer having a comparatively high sensitivity, a yellow filter layer, a blue-sensitive silver halide emulsion layer, a green-sensitive silver halide emulsion layer having a comparatively low sensitivity and a protective layer, at least one of said green-sensitive silver halide emulsion layer having a comparatively low sensitivity, said blue-sensitive silver halide emulsion layer and said protective layer containing at least one compound represented by the general formula (I) as described in claim 1.

7. The silver halide color photographic light-sensitive material as claimed in claim 1, wherein said color photographic light-sensitive material is a multilayer color photographic light-sensitive material comprising a support having thereon an antihalation layer, a gelatin intermediate layer, a blue-sensitive silver halide emulsion layer, a gelatin intermediate layer, a red-sensitive silver halide emulsion layer, a gelatin intermediate layer, a green-sensitive silver halide emulsion layer, a yellow filter layer and a protective layer, at least one of said green-sensitive silver halide emulsion layer, said yellow filter layer and said protective layer containing at least one compound represented by the general formula (I) as described in claim 1.

8. The silver halide color photographic material of claim 1, wherein said color image forming compound is selected from the group consisting of a color coupler, a redox compound which releases a diffusible dye, a coupler which releases a diffusible dye and a dye developer.

9. The silver halide color photographic material of claim 8, wherein said color image forming compound is a color coupler.

10. The silver halide color photographic material of claim 9, wherein said color coupler is at least one compound selected from the group consisting of benzoylacetoanilide type 2-equivalent or 4-equivalent yellow couplers, pivaloylacetoanilide type 2-equivalent or 4-equivalent yellow couplers, pyrazolone type 2-equivalent or 4-equivalent magenta couplers, indazolone type 2-equivalent or 4-equivalent magenta couplers, cyanoacetyl type 2-equivalent or 4-equivalent magenta couplers, phenol type 2-equivalent or 4-equivalent cyan couplers, naphthol type 2-equivalent or 4-equivalent cyan couplers, cyan colored couplers and magenta colored couplers.

* * * * *